United States Patent

Hartog et al.

Patent Number: 5,462,942
Date of Patent: Oct. 31, 1995

[54] 2,3-DIHYDRO-1,4-BENZODIOXIN-5-YL-PIPERAZINE DERIVATIVES HAVING 5-HT1A-ANTAGONISTIC ACTIVITY

[75] Inventors: Jan Hartog; Bartholomeus J. Van Steen; Johannes Mos; Jacques Schipper, all of Weesp, Netherlands

[73] Assignee: Duphar International Research B.V., Weesp, Netherlands

[21] Appl. No.: 269,086

[22] Filed: Jun. 30, 1994

[30] Foreign Application Priority Data

Jul. 5, 1993 [EP] European Pat. Off. ............. 93201950

[51] Int. Cl.⁶ .................. A61K 31/495; C07D 405/14
[52] U.S. Cl. .................. 514/254; 544/364; 544/368; 544/373
[58] Field of Search ................ 544/368, 373, 544/364; 514/254

[56] References Cited

U.S. PATENT DOCUMENTS

| | | | |
|---|---|---|---|
| 4,591,590 | 5/1986 | Ueda et al. | 544/368 |
| 4,833,142 | 5/1989 | Hartos et al. | 544/368 |
| 5,001,130 | 3/1991 | New et al. | 544/368 |

FOREIGN PATENT DOCUMENTS

| | | | |
|---|---|---|---|
| 0084993 | 8/1983 | European Pat. Off. | |
| 0100200 | 2/1984 | European Pat. Off. | |
| 0190472 | 8/1986 | European Pat. Off. | |
| 0236930 | 9/1987 | European Pat. Off. | |
| 0372657 | 6/1990 | European Pat. Off. | |
| 0376607 | 7/1990 | European Pat. Off. | |
| 0529462 | 3/1992 | European Pat. Off. | |
| 3726425 | 9/1988 | Germany | |
| 2184667 | 7/1990 | Japan | 544/368 |
| 16073 | 8/1993 | WIPO | 544/368 |

*Primary Examiner*—Cecilia Tsang
*Attorney, Agent, or Firm*—Stevens, Davis, Miller & Mosher

[57] ABSTRACT

The present invention is concerned with compounds having 5-HT1A antagonistic activity useful in treating CNS disorders and having formula 2

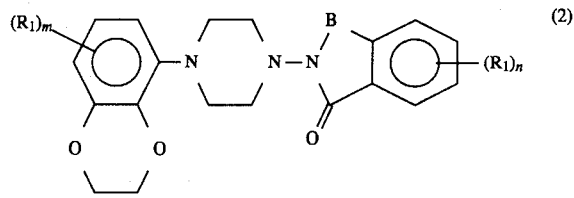

wherein
$R_1$ is halogen, lower alkyl or alkoxy, hydroxy, trifluotomethyl or cyano,
m has the value 1 or 2 and n has the value 0 or 1,
A represents an alkylene chain containing 2–6 C-atoms which may be substituted with one or more lower alkyl groups or a monocyclic (hetero)aryl group, and
B is methylene, ethylene, carbonyl, sulfinyl, sulfonyl or sulfur, and salts thereof.

3 Claims, No Drawings

2,3-DIHYDRO-1,4-BENZODIOXIN-5-YL-PIPERAZINE DERIVATIVES HAVING 5-HT1A-ANTAGONISTIC ACTIVITY

The invention relates to a group of new 2,3-dihydro-1,4-benzodioxin-5-yl-piperazine derivatives with interesting pharmacological properties, to the preparation of these compounds and to compositions containing at least one of these compounds or a salt thereof as an active component.

European patent No. 0190472 relates to compounds of the formula (1)

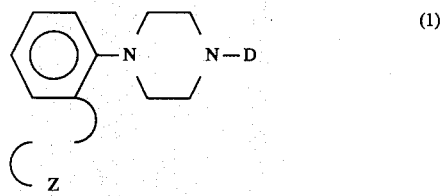

wherein Z together with the phenyl group preferably represents an optionally substituted benzofuranyl group or benzodioxolyl group, and D may represent an alkyl chain optionally substituted with a phenyl group, hetero-aryl group or heterocyclic group.

It is described that these compounds have interesting psychotropic properties, and more particularly have antipsychotic properties.

Is has now been found that compounds of the formula (2)

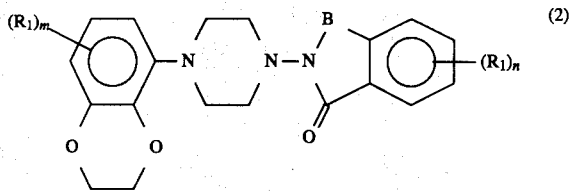

wherein $R_1$ is halogen, lower alkyl or alkoxy, hydroxy, trifluoromethyl or cyano, m has the value 1 or 2 and n has the value 0 or 1, A represents an alkylene chain containing 2–6 C-atoms which may be substituted with one more lower alkyl groups or a monocyclic (hetero)aryl group, and B is methylene, ethylene, carbonyl, sulfinyl, sulfonyl, or sulfur, and salts thereof have a selective 5-HT$_{1-A}$-antagonistic activity.

Lower alkyl and alkoxy groups are groups having 1–4 C-atoms which chains may be straight or branched.

Suitable acids with which the compounds of formula (2) can form pharmaceutically acceptable acid addition salts are for example hydrochloric acid, sulfunic acid, phosphoric acid, nitric acid, and organic acids such as citric acid, fumaric acid, maleic acid, tartaric acid, acetic acid, benzoic acid, p-toluenesulfonic acid, methanesulfonic acid, naphtalenesulfonic acid and the like.

When alkylene chain A is substituted a centre of chirality is present in the compounds. The invention both relates to racemic compounds and individual enantiomers.

It has surprisingly been found that these new piperazine derivative of formula (2) and their salts are selective 5-HT$_{1-}$$_A$-antagonists which can be used for the treatment of CNS-disorders in which the serotonergic transmission is disturbed, for example anxiety disorders, depression, psychosis, loss of memory, sleep disturbances, feeding behaviour and sexual dysfunction.

The compounds were tested for their ability to displace [$^3$H]-2-(di-n-propylamino)- 8-hydroxytetralin([$^3$H]-8-OH-DPAT) from its specific binding sites in rat frontal cortex homogenates. This test is based on the method described by Gozlan et al. (Nature, 305, (1983), pages 140–142). In general the compounds bind to the 5-HT$_{1-A}$-receptors in a considerable greater extent than they bind to other receptors such as $D_2$ and $a_1$ receptors and other 5-HT receptors.

Based on this finding the compounds have been tested for their 5-HT$_{1-A}$-receptor antagonism in tests involving the antagonism of 8-OH-DPAT induced effects in rats, e.g. antagonism of hypothermia, lower lip retraction (based on the method described by Broekkamp et al., Pharmacol. Biochem. Behav. 33, (1989), 821–827).

It appears from the pharmacological tests that the compounds according to the invention are selective 5-HT$_{1-A}$-antagonists. Moreover, the compounds when given orally show a good bioavailability, which results in high potency and long duration of action.

The active compounds and their salts can be processed to compositions by means of standard methods, for example pills, tablets, coated tablets, capsules, powders, injection liquids and the like, using auxiliary substances such as liquid and solid carrier materials.

The compounds having formula (2) are new compounds which can be prepared according to methods suitable for structurally related piperazine derivatives.

More particularly these compounds can be obtained by reaction of a compound having formula (3):

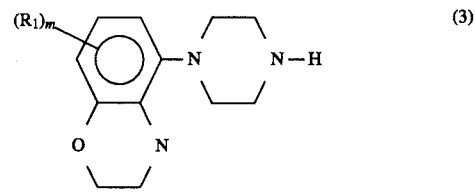

with a compound of the formula (4):

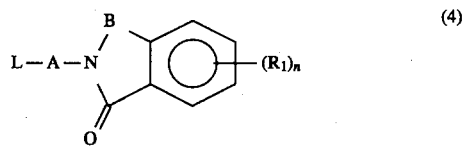

in which formulae $R_1$, m, n, A and B have the meanings given above and L is a so-called leaving group, e.g. a halogen atom or a sulfonate ester group.

This reaction may be carried out both with or without an aprotic organic solvent, optionally in the presence of an acid binder. Examples of suitable solvents are methyl ethyl ketone, tetrahydrofuran, acetonitril, dimethyl formamide, toluene and petroleum ether. As acid binders are to be considered substances which may be soluble or insoluble in the reaction medium, for example, organic nitrogen bases, such as trialkyl amines, pyridine, urea, and inorganic bases, such as sodium or potassium carbonate or -bicarbonate. The reaction temperature usually is between room temperature and the reflux temperature of the solvent used, while the reaction duration may vary from 1 hour to several days.

The starting compounds having formula (3) can be obtained according to methods known for analogous compounds as described in European patent No. 0189612.

The starting compounds having formula (4) are known compounds or can be obtained similar to structurally related known compounds.

3

Further the compounds having formula (2) can be obtained by reacting a compound of the formula (5)

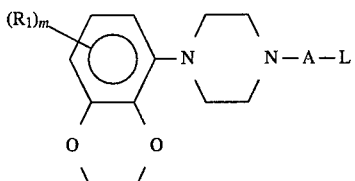

with a compound of the formula (6):

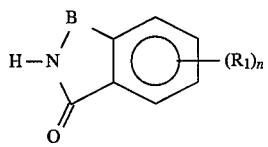

in which formulae $R_1$, m, n, A, B and L have the meanings mentioned above.

This reaction can be carried out under conditions which are usual for this type of coupling reactions.

The starting compounds having formula (5) can be prepared according to methods known for analogous compounds as described for example in European patent No. 0190472.

The compounds having formula (6) are known compounds or can be prepared analogous to known compounds.

The compounds having formula (2) can also be prepared by reaction of a compound of the formula (7)

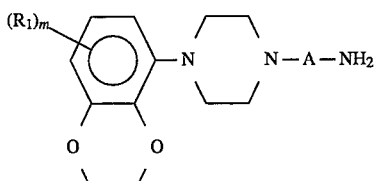

with a compound of the formula (8)

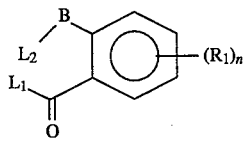

in which formulae $R_1$, m, n, A and B have the meanings given above, and $L_1$ and $L_2$ may be identical or different and have the meanings given for L above.

This reaction can be carried out under the same circumstances as mentioned above for the reaction of compound (3) with compound (4).

Starting compounds of the formula (7) can be obtained from compounds having above formula (3) by means of standard chemical procedures, e.g. by reaction of a compound (3) with chloro-acetonitrile or chloro-propionitrile using an acid binding agent. This reaction can be carried out for example in acetonitrile or dimethylformamide. The intermediate so obtained can then be reduced to a compound (7) in a manner known per se, for example with lithium aluminium hydride.

Starting compounds (8) are known compounds or can be obtained analogous to known compounds.

The invention will now be illustrated by means of the following specific examples.

4

EXAMPLE 1

2-(2-(4-(7-chloro-2,3-dihydro-1,4-benzodioxin-5-yl)-1-piperazinyl)-ethyl)- 1,2-benzisothiazole-3(2H)-one-1,1-dioxide, hydrochloride To a stirred suspension of sodium hydride (0.31 g, 13 mmol) in 12 ml of dry DMF was added saccharin (2.29 g, 13 mmol) in 12 ml of dry DMF. Stirring was continued for 10 minutes before 1-(7-chloro-2,3-dihydro-1,4-benzodioxin-5-yl)-4-(2-chloroethyl)piperazine (4.12 g, 13 mmol) (which can be obtained as described in EP-A-0190472) in 20 ml of dry DMF was added. The reaction mixture was heated under a nitrogen atmosphere for 7 hours, cooled down and extracted with ethylacetate (3×100 ml). The combined organic layers were washed with 5% $NaHCO_3$, brine, dried and the solvent was removed in vacuo. The crude product was purified by flash column chromatography (silicagel/acetone:hexane=1:3) and the so-obtained free base was converted to its hydrochloride salt. Yield 3.13 g, (50%), m.p. 267°–70° C.

EXAMPLE 2

2-(4-(4-(7-chloro-2,3-dihydro-1,4-benzodioxin-5-yl)-1-piperazinyl)-butyl)-1,2-benzisothiazole-3(2H)-one-1,1-dioxide, mesylate a. The intermediate 1-(7-chloro-2,3-dihydro-1,4-benzodioxin-5-yl)piperazine hydrochloride was obtained analogous to the method described in EP 0189612.

b. The title compound was prepared by the method described for 2-(4-(4-(7-bromo-2,3-dihydro- 1,4-benzodioxin-5-yl)-1-piperazinyl)-butyl)-1,2-benzisothiazole-3(2H)-one-1,1-dioxide, dihydrochloride (Example 3) by using above intermediate a), m.p. 242° C.

EXAMPLE 3

2-(4-(4-(7-bromo-2,3-dihydro-1,4-benzodioxin-5-yl)-1-piperazinyl)-butyl)- 1,2-benzisothiazole-3(2H)-one-1,1-dioxide, dihydrochloride a. The intermediate 1-(7-bromo-2,3-dihydro-1, 4-benzodioxin-5-yl)piperazine hydrochloride was obtained analogous to the method as described in EP 0189612.

b. To a stirred solution of intermediate a (1.68 g, 5.0 mmol) in 50 ml of acetonitrile was added diisopropylethylamine (4.50 ml, 5 eq.) and 2-(4-bromobutyl)-1, 2-benzisothiazole- 3-(2H)-one-1,1-dioxide (1.63 g, 5.1 mmol) (which was synthesized from 1,2-benzisothiazole-3(2H)-one-1,1-dioxide and 1,4-dibromobutane using standard procedures). The mixture was refluxed for 24 hours, cooled down and the solvent was removed in vacuo. Ethylacetate was added (200 ml) and the solution was washed with 2N NaOH (2×50 ml). The organic layer was separated, dried and removed in vacuo. The crude product was purified by flash column chromatography (silicagel/diethylether) and converted to its dihydrochloride salt. Yield 1.60 g (53%), m.p. >177° C. (dec.), $^1$H-NMR (DMSO:$CDCl_3$= 4:1)δ1.78–1.92 (cluster, 4H, $CH_2CH_2CH_2CH_2$), 3.06–3.25 (cluster, 6H), 3.53 (m, 4H, $H_{eq}$ pip$CH_2$), 3.80 (t, 2H, $CH_2CH_2NSO_2$, J=6 Hz), 4.24 (m, 4H, $OCH_2CH_2O$), 6.61 (d, 1H, H-6, J=2 Hz), 6.75 (d, 1H, H-8 J=2 Hz), 7.97–8.13 (cluster, 3H), 8.26 (m, 1H), 10.6 (br, 1H, NH+)

EXAMPLE 4

2-(4-(4-(7-bromo-2,3-dihydro-1,4-benzodioxin-5-yl)-1-piperazinyl)-butyl)- 1H-isoindole-1,3(2H)-dione, dihydrochloride To a stirred solution of intermediate a) of Example 3 (1.75 g, 5.2 mmol) in 75 ml of acetonitrile was added 2-(4-bromobutyl)-1H-isoindole-1,3(2H)-dione (1,76 g, 6.2 mmol). After being refluxed for 3 days the reaction mixture was cooled down and poured into ethylacetate (50 ml) and 2N NaOH (100 ml). The water layer was extracted with ethylacetate (3×50 ml) and the combined organic layers were washed with brine (2×100 ml), dried and evaporated to dryness. After purification by flash column chromatography (silicagel/ethylacetate) the free base was obtained in 76% yield, and converted to its dihydrochloride salt. Yield 1.70 g (59%), m.p. 230°–1° C.

EXAMPLE 5

2-(2-(4-(7-bromo-2,3-dihydro-1,4-benzodioxin-5-yl)-1-piperazinyl)-ethyl)-6-chloro-3,4-dihydroisoquinolin-1(2H)-one, dihydrochloride This compound was obtained analogous to the method described in EP-A-0190472 for 1-(benzo-[b]furan-7-yl)-4-[3-(4-fluorobenzoyl)-propyl)piperazine using 1-(7-bromo-2,3-dihydro-1,4-benzodioxin-5-yl)-4-(2-chloroethyl)piperazine (which was prepared similar to the method described for 1-(7-chloro-2,3-dihydro-1,4-benzodioxin- 5-yl)-4-(2-chloroethyl)piperazine as described in EP-A-0190472), and 6-chloro-3,4-dihydroisoquinolin-1(2H)-one. Yield 37%, m.p. <240° C. (dec.), $^1$H-NMR (DMSO:CDCl$_3$=4:1)δ3.09 (t, 2H, NCH$_2$CH$_2$Ar J=7 Hz), 3.16 (m, 2H, H$_{ax}$ pipCH$_2$), 3.45 (m, 2H, +NCH$_2$CH$_2$), 3.55 (m, 2H, H$_{eq}$ pipCH$_2$), 3.65–3.75 (cluster, 4H), 3.94 (t, 2H, CH$_2$CH$_2$NC=O), 4.26 (m, 4H, OCH$_2$CH$_2$O), 6.62 (d, 1H, H-6, J=2 Hz), 6.75 (d, 1H, H-8 J=2 Hz), 7.37 (cluster, 2H), 7.88 (d, 1H, J=8 Hz), 11.0 (br, 1H, NH+)

EXAMPLE 6

2-(4-(4-(7-chloro-2,3-dihydro-1,4-benzodioxin-5-yl)-1-piperazinyl)-butyl)- 6-chloro-3,4-dihydroisoquinolin-1(2H)-one, dihydrochloride a. To a solution of 6-chloro-3,4-dihydroisoquinolin-1(2H)-one (3.00 g, 17 mmol) in 50 ml of DMF was added sodiumhydride (0.80 g, 60% suspension in mineral oil) at room temperature. Stirring was continued for 3 hours and 10 ml of 1,4-dibromobutane was added at 10° C. The reaction mixture was refluxed for 24 hours, cooled down and poured into ethylacetate and water. The organic layer was separated and washed with water and the solvent was removed in vacuo. After purification by column chromatography (silicagel/ether:hexane=1:1) the intermediate 2-(4-bromobutyl)-6-chloro- 3,4-dihydroisoquinolin-1(2H)-one was obtained.

b. To a stirred solution of intermediate a of example 2 (1.20 g, 3.8 mmol) and diisopropylethylamine (2.00 ml, 12 mmol) in 15 ml of acetonitrile was added intermediate 6a (1.30 g, 4.1 mmol). The reaction mixture was heated under reflux for 2 days, cooled down and then extracted with ethylacetate (3×100 ml). The combined organic layers were washed with water, dried and the solvent was removed in vacuo. The crude product was purified by column chromatography (silicagel/dichloromethane:methanol= 95:5) and the so-obtained free base was converted to its dihydrochloride salt. Yield 1.10 g (52%) of the title compound, m.p. 214°–6° C.

EXAMPLE 7

2-(4-(4-(7-chloro-2,3-dihydro-1,4-benzodioxin-5-yl)-1-piperazinyl)- 3-methyl-butyl)-1,2-benzisothiazole-3(2H)-one-1,1-dioxide, dihydrochloride a. A stirred solution of 1-bromo-3-methyl-3-butene (8.00 g, 54 mmol) (which can be obtained as described in J. Org. Chem., 46, 1981, 3526–30), saccharin (9.90 g, 54 mmol) and diisopropylethylamine (9.40 ml, 54 mmol) in 50 ml of acetonitrile was refluxed under a nitrogen atmosphere for 18 hours. The reaction mixture was concentrated in vacuo, extracted with ethylacetate and the combined organic layers were washed with water. The crude intermediate 2-(3-methyl-3-butenyl)-1,2-benzisothiazole-3(2H)-one-1,1-dioxide was further purified by flash column chromatography (silicagel/ether:hexane=1:3)

b. Intermediate a (0.50 g, 2.0 mmol) was dissolved in 80 ml of pentane under a nitrogen atmosphere. Treatment of the solution with HBr analogous to the method described in J. Org. Chem., 47(27), 1982, 5378 and J.A.C.S., 109(23), 1897, 6943 resulted in 0.54 g (81%) of the intermediate 2-(4-bromo-3-methyl-butyl)-1,2-benzisothiazole-3(2H)-one-1,1-dioxide.

c. To a stirred solution of intermediate 2a (2.1 g, 7.2 mmol) in 75 ml of acetonitrile was added intermediate 7b (2.14 g, contained 7.2 mmol) and diisopropylethylamine (2.60 ml, 15 mmol). After being refluxed for 3 days the reaction mixture was cooled down and concentrated in vacuo. The residue was taken up in ethylacetate and washed with water, dried and the solvent was removed in vacuo. The crude product was purified by column chromatography (silicagel/hexane:ethylacetate=1:1) and the so-obtained free base was converted to the title compound. Yield 1.00 g (33%), m.p. 210°–2° C.

EXAMPLE 8

2-(4-(4-(7-chloro-2,3-dihydro-1,4-benzodioxin-5-yl)-1-piperazinyl)-butyl)- 1H-isoindole-1,3(2H)-dione, hydrochloride This compound was prepared analogous to the method described for 2-(4-(4-(7-bromo-2,3-dihydro- 1,4-benzodioxin-5-yl)-1-piperazinyl)-butyl)-1H-isoindole- 1,3(2H)-dione, dihydrochloride (Example 3) using intermediate 2a (1.30 g, 4.5 mmol) and 2-(4-bromobutyl)-1H-isoindole-1, 3(2H)-dione (1.40 g, 4.9 mmol). Yield 2.20 g, m.p. 222°–4° C.

EXAMPLE 9

2-(5-(4-(7-chloro-2,3-dihydro-1,4-benzodioxin-5-yl)-1-piperazinyl)-pentyl)- 1,2-benzisothiazole-3(2H)-one-1,1-dioxide, hydrochloride This compound was prepared analogous to the method described for 2-(4-(4-(7-bromo-2,3-dihydro-1,4-benzodioxin-5-yl)-1-piperazinyl)-butyl)- 1,2-benzisothiazole-3(2H)-one-1,1-dioxide, dihydrochloride (Example 3) using intermediate 2a (2.00 g, 6.9 mmol) and 2(5-bromopentyl)-1,2-benzisothiazole-3(2H)-one-1,1-dioxide (2.52 g, 7.6 mmol). Yield 1.40 g, m.p. 193°–5° C.

EXAMPLE 10

2-(4-(4-(7-hydroxy-2,3-dihydro-1,4-benzodioxin-5-yl)-1-piperazinyl)-butyl)- 1,2-benzisothiazole-3(2H)-one-1,1-dioxide a. To a stirred suspension of intermediate 3a (6.77 g, 20 mmol) in 50 ml of dry DMF was added potassium carbonate (5.60 g, 41 mmol) and benzylbromide (2.60 ml, 22 mmol). Stirring was continued at 85° C. for 18 hours. The reaction mixture was cooled down, poured into ice and taken up in ethylacetate, washed with water, dried and the solvent was removed in vacuo. The crude product was purified by column chromatography (silicagel/ethylacetate:methanol:ammonia=92.5: 7: 0.5) Yield: 7.18 g (91%) of the intermediate 4-benzyl-1-(7-bromo-2,3-dihydro-1,4-benzodioxin- 5-yl)piperazine.

b. The bromo derivative intermediate 10a was converted to the corresponding hydroxy derivative by the method described in J. Org. Chem., 48(12), 1983, 1941–4 and Chem. Ber., 103, 1970, 1412–9 using intermediate 10a (6.68 g, 17 mmol), tetramethylethylenediamine (1.40 ml, 17 mmol), n-butyllithium (10.3 ml (2.5M), 26 mmol), nitrobenzene (5.30 ml, 52 mmol). Purification of the crude product by column chromatography (silicagel/ether:hexane=3: 1) resulted in the free base of the intermediate 4-benzyl-1-(7-hydroxy-2,3-dihydro-1,4-benzodioxin-5-yl)piperazine in 48% yield.

c. Debenzylation of intermediate 10b using 10% Pd/C and ammoniumformiate in methanol afforded the intermediate 1-(7-hydroxy-2,3-dihydro-1,4-benzodioxin-5-yl)piperazine in 89% yield after purification by column chromatography (silicagel/tetrahydrofuran:methanol:ammonia=83:15:2).

d. Intermediate 10c was converted to the title compound by the method described for 2-(4-(4-(7-bromo-2,3-dihydro-1,4-benzodioxin-5-yl)-1-piperazinyl)-butyl)-1,2-benzisothiazole-3(2H)-one-1,1-dioxide, dihydrochloride (Example 3) using intermediate 10c (1.70 g, 7.2 mmol), sodiumacetate (1.20 g, 15.0 mmol), 2-(4-bromobutyl)-1,2-benzisothiazole-3(2H)-one-1,1-dioxide (2.50 g, 7.9 mmol), in 75 ml of acetonitrile. The crude product was purified by column chromatography (silicagel/dichloromethane:methanol=95: 5) and the resulting foam was crystallized from ethylacetate. Yield 1.73 g (51%), m.p. 179°–181° C.

EXAMPLE 11

2-(4-(4-(7-chloro-2,3-dihydro-1,4-benzodioxin-5-yl)-1-piperazinyl)-butyl)- 2,3-dihydro-1H-isoindole-1-one, hydrochloride a. To a stirred solution of intermediate 2a (6.40 g, 22 mmol) in 80 ml of acetonitrile was added triethylamine (6.60 g, 66 mmol) and 4-bromobutyronitrile (3.90 g, 26 mmol). The reaction mixture was refluxed for 24 hours, cooled down, concentrated in vacuo. To the residue was added ethylacetate and water. The organic layer was separated and washed with water, dried and concentrated to dryness. The crude product was purified by column chromatography (silicagel/dichloromethane:methanol–98:2). Yield 6.80 g (96%) of the intermediate 1-(7-chloro-2,3-dihydro-1,4-benzodioxin-5-yl)-4-(3-cyanopropyl)piperazine.

b. Intermediate 11a (6.80 g, 21 mmol) was dissolved in 140 ml of 96% ethanol and potassiumhydroxide (0.85 g, 11 mmol) in 7 ml of water was added. Raney-Ni was added and the mixture was stirred under a hydrogen atmosphere at room temperature for 24 hours. The reaction mixture was filtered over hyflo and ethanol was removed in vacuo. The residue was taken up in dichloromethane and washed with water, dried and the solvent was removed in vacuo. The crude product was purified by column chromatography (silicagel/dichloromethane:methanol:ammonia=85:14: 1). Yield 2.50 g (36%) of the intermediate 1-(7-chlor0-2,3-dihydro-1,4-benzodioxin-5-yl)-4-(4-aminobutyl)piperazine.

c. To a stirred suspension of intermediate 11 b (0.33 g, 1.0 mmol) in 10 ml of acetone was added potassium hydroxide (0.34 g (85%), 6.0 mmol) and o-bromomethylene-benzoylchloride (0.23 g, 1.0 mmol). The reaction mixture was heated at reflux for 24 hours, concentrated in vacuo and the residue taken up in dichloromethane. Water was added and the organic layer was separated, washed with water, dried and the solvent was removed in vacuo. The crude product was purified by column chromatography (silicagel/dichloromethane:methanol=95:5). Yield 0.20 g (45%), m.p. 241°–2° C.

EXAMPLE 12

2-(4-(4-(7-methoxy-2,3-dihydro-1,4-benzodioxin-5-yl)-1-piperazinyl)-butyl)- 1,2-benzisothiazole-3(2H)-one-1,1-dioxide, fumarate a. To a stirred solution of intermediate 10c (2.60 g, 11 mmol) in 200 ml of dichloromethane was added potassium carbonate (4.60 g, 33 mmol). The mixture was cooled to 4° C. and t-butyloxycarbonyl anhydride (3.60 g, 17 mmol) was added. Stirring was continued at room temperature for 1,5 hour. 2N sodium hydroxide and ethanol were added and stirring was continued for 1 hour. The mixture was extracted with ethyl acetate and the combined organic layers were washed with 5% sodium bicarbonate, water, dried and the solvent was removed in vacuo. Yield: 1.70 g (47%) of the intermediate 1-(7-hydroxy-2,3-dihydro-1,4-benzodioxin-5-yl)-4-(t-butyloxycarbonyl)piperazine.

b. To a stirred solution of intermediate 12a (1.70 g, 5.1 mmol) and potassium carbonate (1.40 g, 10 mmol) in 50 ml of acetonitrile was added methyliodide (0.65 ml, 10 mmol). The reaction mixture was heated at 40° C. for 18 hours, cooled down, concentrated and the crude product was purified by column chromatography (aluminum oxide/ether). Yield 0.71 g (57%) of 1-(7-methoxy-2,3-dihydro-1,4-benzodioxin-5-yl)- 4-(t-butyloxycarbonyl)piperazine.

c. To a solution of intermediate 12b (1.00 g, 3.0 mmol) in 25 ml of ethylacetate was added 25 ml of ethanol containing 5 eq of hydrochloric acid. The reaction mixture was stirred for 18 hours at room temperature and the solvent was removed in vacuo. Obtained was 0.80 g of the intermediate 1-(7-methoxy-2,3-dihydro-1,4-benzodioxin-5-yl)piperazine hydrochloride.

d. Intermediate 12c (0.80 g, 2.8 mmol) was converted to the title compound as described for 2-(4-(4-(7-bromo-2,3-dihydro-1,4-benzodioxin-5-yl)-1-piperazinyl)-butyl)- 1,2-benzisothiazole-3(2H)-one-1,1-dioxide, dihydrochloride (Example 3). Purification of the crude product was carried out by column chromatography (silicagel/ethyl acetate). Yield:0.90 g (54%), m.p. 74°–7° C.

EXAMPLE 13

2-(4-(4-(7 -cyano-2,3-dihydro-1,4-benzodioxin-5-yl)-1-piperazinyl)-butyl)- 1,2-benzisothiazole-3(2H)-one-1,1-dioxide a. The intermediate 1 -(7-bromo-2,3-dihydro-1,4-benzodioxin-5-yl)-4-(t-butyloxycarbonyl)piperazine was prepared similar to the method described for 1-(7-hydroxy-2,3-dihydro-1,4-benzodioxin-5-yl)-4-(t-butyloxycarbonyl)piperazine (Intermediate 12a) using 1-(7-bromo-2,3-dihydro-1,4-benzodioxin-5-yl)piperazine.

b. To a stirred solution of intermediate 13a (4.10 g, 10 mmol) in 100 ml of toluene was added palladium(0)tetrakis triphenylphosphine (4.20 g, 2.1 mmol) and sodium cyanide (6.00 g, 12 mmol [suspended on 12 g of aluminum oxide]). The reaction mixture was heated at 110° C. for 18 hours, cooled down and concentrated in vacuo. The residue was purified by column chromatography (silicagel/ ether: hexane=1:1). Yield:1.90 g (54%) of the intermediate 1-(7-cyano-2,3-dihydro-1,4-benzodioxin-5yl)-4-(t-butyloxycarbonyl)piperazine.

c. Intermediate 13b (1.90 g, 5.5 mmol) was converted into 1-(7-cyano-2,3-dihydro- 1,4-benzodioxin-5-yl)-4-piperazine by reaction with trimethylsilyliodide (1.20 ml, 8.4 mmol) in 75 ml of acetonitrile at 4° C. The residue obtained after removal of the solvent in vacuo was purified by column chromatography (silicagel/ethylacetate: methanol: ammonia=83:15:2). Yield: 1.25 g (93%).

d. Intermediate 13c (1.25 g, 5.1 mmol) was converted to title compound by the method described for 2-(4-(4-(7-bromo-2,3-dihydro-1,4-benzodioxin 5-yl)- 1-piperazinyl)-butyl)-1,2-benzisothiazole-3(2H)-one-1,1-dioxide, dihydrochloride (Example 3). Purification of the crude product by column chromatography (silicagel/ ethyl acetate). Yield: 2.11 g (86%), m.p. 162°–4° C.

EXAMPLE 14

2-(4-(4-(7 -chloro-8-methyl-2,3-dihydro-1,4-benzodioxin-5-yl)- 1-piperazinyl)-butyl)-1,2-benzisothiazole- 3(2H)-one-1,1-dioxide a. The intermediate 4-benzyl-1 -(7-chloro-2,3-dihydro-1, 4-benzodioxin-5-yl)piperazine was obtained by the method as described for 4-benzyl-1-(7-bromo- 2,3-dihydro-1,4-benzodioxin-5-yl)piperazine (intermediate 10a). Purification of the crude product was carried out by flash column chromatography (silicagel/ethylacetate:methanol:ammonia=83:15 2).

b. To a stirred solution of intermediate 14a (7.30 g, 21 mmol) in 100 ml of toluene was added tetramethylethylenediamine (1.73 ml, 21 mmol). The mixture was cooled to −78° C. and n-butyllithium (11.0 ml (2.5M), 28 mmol) was added. After stirring at −78° C. for 3.5 hours dimethylformamide (4.90 ml, 64 mmol) was added. Stirring was continued at −78° C. for 45 min. and 45 min. at room temperature. The reaction mixture was hydrolysed with 20 ml of 2N hydrochloric acid for 1 hour, 20 ml of 2N sodiumhydroxide was added and the mixture was extracted with ethyl acetate. The combined organic layers were washed with water, dried, and the solvent was removed in vacuo. The crude product was purified by column chromatography (silicagel/ethyl acetate:hexane=1:1) resulting in the intermediate 4-benzyl-1-(7-chloro 8-formyl-2,3-dihydro-1,4-benzodioxin-5-yl) piperazine.

c. To a stirred suspension of intermediate 14b (4.38 g, 12 mmol) in 75 ml of methanol was added at 0° C. sodium boronhydride (1.34 g, 35 mmol). After 30 minutes the mixture was poured into ethyl acetate and 5% sodium bicarbonate. The organic layer was separated and washed with water, dried and the solvent was evaporated. This residue was dissolved in 30 ml of dichloromethane and added dropwise to a solution of triethylsilylhydride (5.60 ml, 35 mmol), trifluoroacetic acid (2.70 ml, 35 mmol) in 25 ml of dichloromethane. After 2 hours the reaction mixture was extracted with ethyl acetate and washed with 5% of sodium bicarbonate. The combined organic layers were washed with water, dried and the solvent was removed in vacuo. The crude product was purified by column chromatography (silicagel/ether) giving 4.02 g (81%) of the intermediate 4-benzyl-1-(7-chloro-8-methyl-2,3-dihydro-1,4-benzodioxin-5-yl)piperazine.

d. Intermediate 14c (4.03 g, 11 mmol) was debenzylated by using a-chloroethyl chloroformate (1.35 ml, 12 mmol), 100 ml of 1,2 dichloroethane. The mixture was heated at 80° C. for 2 hours, the solvent removed in vacuo. To the residue 100 ml of methanol was added and stirring at reflux temperature was continued for 1 hour. The reaction mixture was concentrated and the residue was stirred with diisopropylether. The solid was filtered off giving 3.02 g (88%) of the intermediate 1 -(7-chloro-8-methyl-2,3-dihydro-1,4-benzodioxin-5-yl)piperazine hydrochloride.

e. Intermediate 14d (3.02 g, 9.9 mmol) was converted to the title compound by the method described for 2-(4-(4-(7-bromo-2,3-dihydro-1,4-benzodioxin- 5-yl)-1-piperazinyl)-butyl)-1,2-benzisothiazole-3(2H)-one-1, 1-dioxide, dihydrochloride (Example 3). Yield:3.68 g (64%), m.p. 136°–7° C.

EXAMPLE 15

2-(4-(4-(7 -chloro-2,3-dihydro-1,4-benzodioxin-5-yl)-1-piperazinyl)- 2,2-dimethylbutyl)-1,2-benzisothiazole-3(2H)-one-1,1-dioxide, dihydrochloride a. The intermediate 1-(7-chloro-2,3-dihydro-1,4-benzodioxin-5-yl)-4-(4-amino-3,3-dimethylbutyl)piperazine was prepared analogous to the method described for 1-(7-chloro-2,3-dihydro-1,4-benzodioxin-5-yl)-4-(4-aminobutyl)piperazine (Intermediate 11b) using 4-chloro-2,2-dimethylbutyronitrile.

b. To a stirred solution of intermediate 15a (1.10 g, 3.1 mmol) in 40 ml of acetonitrile was added methyl o-chlorosulfonylbenzoate (0.73 g, 3.1 mmol) in 5 ml of methanol. The reaction mixture was stirred at room temperature for 1 hour and the solvent was removed in vacuo. The crude product was purified by column chromatography (silicagel/dichloromethane:methanol= 97: 3). Yield: 1.30 g (76%) of the intermediate N-(4-(4-(7-chloro-2,3dihydro-1,4-benzodioxin-5-yl)-1-piperazinyl)- 2,2-dimethyl-butyl)-2-methyloxycarbonylphenylsulfonamide.

c. Intermediate 15b (1.15g, 2.1 mmol) was solved in 25 ml of methyl ethyl ketone. Potassium carbonate (0.58 g, 4.2 mmol) was added and the mixture was refluxed for 3 hours, the solvent was removed in vacuo and the residue was purified by column chromatography (silicagel/dichloromethane:methanol=97: 3). Yield: 1.10 g (94%) of the title compound, m.p. 260°–2° C.

EXAMPLE 16

2-(4-(4-(6-chloro-2,3-dihydro-1,4-benzodioxin-5-yl)-1-piperazinyl)-butyl)- 1,2-benzisothiazole-3(2H)-one-1,1-dioxide, dihydrochloride a. To a stirred solution of 1-(2,3-dihydro-1,4-benzodioxin-5-yl)piperazine (7.4 g, 33 mmol) in 100 ml of dichloromethane was added a catalytic amount of aluminum trichloride and diphenylsulfide. The mixture was cooled to 10° C. and sulfuryl chloride (2.65 ml, 33 mmol) was added. Stirring was continued for 24 hours at room temperature, the solvent was removed in vacuo. To the residue was added dichloromethane and 2N sodium hydroxide. The organic layer was washed with water, dried and the solvent was removed. The residue contained 17 mol % of the intermediate 1-(6-chloro-2,3-dihydro-1,4-benzodioxin-5-yl)-piperazine which was isolated using HPLC.

b. The title compound was obtained by the method described for 2-(4-(4-(7-bromo- 2,3-dihydro-1,4-benzodioxin-5-yl)-1-piperazinyl)-butyl)-1H-isoindole-1, 3(2H)-dione, dihydrochloride (Example 3) using intermediate 16a (1.42 g, 5.6 mmol), 2-(4-bromobutyl)-1, 2-benzisothiazole-3(2H)-one-1,1-dioxide (1.80 g, 5.6 mmol), triethylamine (1.50 ml, 11 mmol) and sodium iodide (0.84 g, 5.6 mmol) in 30 ml of acetonitrile. The crude product was purified by column chromatography (silicagel/dichloromethane:methanol=97:3). Yield:0.21 g (7%), m.p. 211°–3° C.

EXAMPLE 17

2-(4-(4-(8-chloro-2,3-dihydro-1,4-benzodioxin-5-yl)-1-piperazinyl)-butyl)- 1,2-benzisothiazole-3(2H)-one-1,1-dioxide, dihydrochloride a. The intermediate 1-(8-chloro-2,3-dihydro-1,4-benzodioxin-5-yl)piperazine was isolated from reaction mixture 16a (which contained 24 mol % of this product) as described for intermediate 16a.

b. The title compound was obtained by the method described for 2-(4-(4-(7-bromo-2,3-dihydro- 1,4-benzodioxin-5-yl)-1-piperazinyl)-butyl)-1H-isoindole-1, 3(2H)-dione, dihydrochloride (Example 3) using intermediate 17a (0.87 g, 3.4 mmol), 2-(4-bromobutyl)-1, 2-benzisothiazole-3(2H)-one-1,1-dioxide (1.10 g, 3.4 mmol), triethylamine (0.94 ml, 6,8 mmol) and sodium iodide (0.51 g, 3.4 mmol) in 25 ml of acetonitrile. The crude product was purified by column chromatography (silicagel/dichloromethane:methanol=97: 3). Yield: 0.72 g (37%), m.p. 204°–5° C.

EXAMPLE 18

2-(4-(4-(7-chloro-2,3-dihydro-1,4-benzodioxin-5-yl)-1 -piperazinyl)-butyl)- 6-chloro-1,2-benzisothiazole-3(2H)-one, dihydrochloride a. Iodine was added to a suspension of diphenyldisulfide-2,2'-dicarboxylic acid dichloride (2.0 g, 5.8 mmol) (which was obtained as described in Beilstein H10:132) in 10 ml of tetrachloromethane. Chlorine gas was added for 15 minutes at a temperature of 30° C. The reaction mixture was stirred for 1 hour at room temperature and the precipitate filtered off and dried. At this reaction temperature, a mixture of 2-(sulfenic acid chloride)-benzoic acid chloride (70%) and 6-chloro-2-(sulfenic acid chloride)-benzoic acid chloride (30%) was formed. At a reaction temperature of 10° C. only 2-(sulfenic acid chloride) benzoic acid chloride is formed in 100% yield.

b. To a stirred suspension of 1-(7-chloro-2,3-dihydro-1, 4-benzodioxin-5-yl)-4-(4-aminobutyl)piperazine (intermediate 11 b) in 10 ml of dichloromethane was added 6-chloro-2-(sulfenic acid chloride)-benzoic acid chloride (1.9 g, contained 1.74 mmol). The suspension was stirred for 18 hours and a solution of 10% potassium carbonate was added. The organic layer was washed with water, dried and further purified by flash column chromatography (silicagel/dichloromethane:methanol=97:3) and converted to its dihydrochloride salt. Yield: 0.47 g (48%) of the title compound, m.p. 207°–9° C.

EXAMPLE 19

2-(4-(4-(7-chloro-2,3-dihydro-1,4-benzodioxin-5-yl)-1-piperazinyl)-butyl) 1,2-benzisothiazole-3(2H)-one-1-oxide, dihydrochloride a. To 2-(sulfenic acid chloride)-benzoic acid chloride (obtained as described in example 18) (7.6 g, 36 mmol) in 100 ml of dry ether was added ammonia gas during 15 minutes. The reaction mixture was stirred at room temperature for 1 hour and the solid was isolated and further purified by column chromatography (silicagel/dichloromethane:methanol=98:2). Yield: 5.30 g (96%) of the intermediate 1,2-benzisothiazole-3(2H)-one.

b. To a stirred solution of intermediate 19a (5.30 g, 35 mmol) in 150 of methanol was added sodium periodate (17.6 g, 82 mmol) in 30 ml of water. The reaction mixture was stirred at room temperature for 78 hours and the solvent was removed in vacuo. The residue was dissolved in dichoromethane and washed with water, dried and concentrated to dryness. Yield: 3.20 g (55%) of the intermediate 1,2-benzisothiazole-3(2H)-one-1-oxide.

c. The intermediate 19b was converted to 2-(4-chlorobutyl)-1,2-benzisothiazole- 3(2H)-one-1-oxide according to the Mitsunobu reaction using triphenylphosphine and diethyl azodicarboxylate by means of standard procedures. The crude product was purified by column chromatography (silicagel/dichloromethane:methanol= 99:1 ).

d. The title compound was obtained analogous to the method described for 2-(4-(4-(7-bromo-2,3-dihydro-1, 4-benzodioxin-5-yl)-1-piperazinyl)-butyl)-1,2-benzisothiazole-3(2H)-one-1,1-dioxide, dihydrochloride (Example 3) using 1-(7-chloro-2,3-dihydro-1,4-benzodioxin-5-yl)piperazine (intermediate 2a) (2.50 g, 8.54 mmol) and 2-(4-chlorobutyl)-1,2-benzisothiazole-3(2H)-one- 1-oxide (Intermediate 19c) (2.20 g, 8.54 mmol). Yield: 1.90 g (41%) of the title compound, m.p. 258°–60° C.

EXAMPLE 20

2-(4-(4-(7-chloro-2,3-dihydro-1,4-benzodioxin-5-yl)-1-piperazinyl)-3-phenylbutyl)- 1,2-benzisothiazole-3(2H)-one-1, 1-dioxide, dihydrochloride a. To a stirred solution of tropic acid (50.g g, 0.30 mol) in 650 ml of water was added barium hydroxide octahydrate (140.0 g, 0.44 mol). The mixture was stirred at reflux temperature for 20 hours and cooled down. To the filtrate was added concentrated hydrochloric acid and the so-obtained suspension was stirred at 0° C. for 2 hours, the solid was filtered off, washed with water and dried. Yield: 36.2 g (81%) of the intermediate 2-phenyl-propenic acid.

b. To a stirred solution of 1-(7-chloro-2,3-dihydro-1,4-benzodioxin-5-yl)piperazine (Intermediate 2a) (43.7 g, 0.17 mol) in 500 ml of ethanol was added 2-phenyl-propenic acid (Intermediate 20a) (25.2 g, 0.17 mol). The reaction mixture was heated at reflux temperature for 78 hours and cooled down. The precipitate was filtered off and washed with ethanol. The crude product was further purified by column chromatography (silicagel/ethyl acetate:methanol:ammonia=75:20:5). Yield: 20.4 g (30%) of the intermediate 3-(1-(7-chloro-2,3-dihydro-1,4-benzodioxin- 5-yl)-piperazinyl)2-phenyl-propionic acid.

c. Intermediate 20b was converted to 1-(7-chloro-2,3-dihydro-1,4-benzodioxin- 5-yl)-4-(2-phenyl-propanol)piperazine (8.7 g, 22 mmol) using lithium aluminumhydride in tetrahydrofuran at 50° C. The crude product was purified by column chromatography (silicagel/dichloromethane:methanol=98:2). Yield: 5.40 g (64%).

d. To a stirred solution of intermediate 20c (5.1 g, 13 mmol) in 80 ml of chloroform was added thionyl chloride (6.3 g, 52 mmol). The mixture was heated at reflux temperature for 5 hours and the solvent was removed in vacuo. 100 ml of 1N sodium hydroxide was added and the mixture was extracted with dichloromethane. The organic layers were combined, washed with water, dried and the solvent was removed. The residu was purified by column chromatography (silicagel/ethylacetate:hexane=1:1). Yield: 4.80 g (90%) of the intermediate 1-(7-chloro-2,3-dihydro-1,4-benzodioxin- 5-yl)-4-(3-chloro-2-phenyl-propyl)piperazine.

e. Intermediate 20d (4.8 g, 12 mmol) was converted to 1-(7-chloro-2,3-dihydro- 1,4-benzodioxin-5-yl)-4-(3-cyano-2-phenyl-propyl)piperazine using potassium cyanide, 18-crown-6, sodium iodide in acetonitrile according to standard procedures. The crude product was purified by column chromatography (silicagel/dichloromethane:methanol=98:2). Yield:3.40 g (73%).

f. Intermediate 20e (3.4 g, 8.6 mmol) was reduced to 1-(7-chloro-2,3 -dihydro-1,4-benzodioxin-5-yl)-4-(4-amino-2-phenyl-butyl)piperazine using hydrogen, Raney-Ni, potassium hydroxide in ethanol/water. The crude product was purified by flash column chromatography (silicagel/dichloromethane:methanol:ammonia=92:7.5:0.5). Yield: 0.50 g (15%).

g. The title compound was obtained by reaction of intermediate 20f (0.5 g, 1.3 mmol) with methyl o-(sulfonyl chloride)benzoate (0.29 g, 1.3 mmol) and triethylamine (0.25 g, 2.5 mmol) in acetonitrile. The reaction was stirred at room temperature for 24 hours, the solvent was removed in vacuo and the crude product was purified using dry column chromatography (silicagel/dichloromethane:methanol=99:1) and converted to its dihydrochloride salt. Yield: 0.41 g (60%), m.p. 212°–4° C.

EXAMPLE 21

2-(4-(4-(7-chloro-2,3-dihydro-1,4-benzodioxin-5-yl)-1-piperazinyl)-butyl)- 5-chloro-1,2-benzisothiazole-3(2H)-one-1,1-dioxide, dihydrochloride a. The intermediate 2-(4-bromobutyl)-5-chloro-1,2-benzisothiazole-3(2H) one-1,1-dioxide was obtained analogous to the method described for 2-(4-bromobutyl)- 1,2-benzisothiazole-3(2H)-one-1,1-dioxide (see Example 3, intermediate 3b) using 1,4-dibromobutane and 5-chloro 1,2-benzisothiazole- 3(2H)-one-1,1-dioxide.

b. The title compound was obtained analogous to the method described for 2-(4-(4-(7-bromo-2,3-dihydro-1,4-benzodioxin-5-yl)-1-piperazinyl)-butyl)-1,2-benzisothiazole-3(2H)-one-1,1-dioxide, dihydrochloride (Example 3) using intermediate 2a (1.0 g, 3.4 mmol), intermediate 21a (1.32 g, 3.8 mmol) and diisopropyl ethyl amine (1.00 g, 1.4 mmol) in 15 ml of acetonitrile. The crude product was purified by column chromatography (silicagel/dichloromethane:methanol=97:3) and converted to its dihydrochloride salt. Yield: 1.88 g (91%), m.p. 190°–2° C.

EXAMPLE 22

2-(4-(4-(7-chloro-2,3-dihydro-1,4-benzodioxin-5-yl)-1-piperazinyl)-butyl)- 1,2-benzisothiazole-3(2H)-one, dihydrochloride The title compound was obtained by the method described for 2-(4-(4-(7-chloro- 2,3-dihydro-1,4-benzodioxin-5-yl)-1-piperazinyl)-butyl)-6-chloro-1,2-benzisothiazole- 3(2H)-one, dihydrochloride (Example 18) using 2-(sulfenic acid chloride)-benzoic acid chloride which was obtained as described for intermediate 18a. m.p 243°–5° C.

We claim:
1. A compound of formula 2

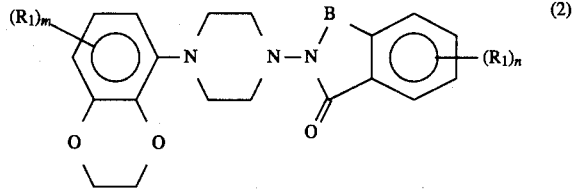

wherein $R_1$ is halogen, lower alkyl or alkoxy, hydroxy, trifluoromethyl or cyano, m has the value 1 or 2 and n has the value 0 or 1, A represents an alkylene chain containing 2–6 C-atoms which may be substituted with one or more lower alkyl groups or a phenyl group, and B is methylene, ethylene, carbonyl, sulfinyl, sulfonyl or sulfur or a pharmaceutically acceptable salt thereof.

2. Pharmaceutical compositions having selective 5-HT$_{1A}$-antagonistic activity which contain a 5-HT$_{1A}$-antagonistically effective amount at least one compound or pharmaceutically acceptable salt as claimed in claim 1 as an active component.

3. A method of treating CNS disorders in which the serotonergic transmission is disturbed, characterized in that a compound as claimed in claim 1 is used.

* * * * *

UNITED STATES PATENT AND TRADEMARK OFFICE
CERTIFICATE OF CORRECTION

PATENT NO. : 5,462,942
DATED : October 31, 1995
INVENTOR(S) : HARTOG et al

It is certified that error appears in the above-indentified patent and that said Letters Patent is hereby corrected as shown below:

In the Abstract on the title page, in column 1, and in claim 1, in column 14, change formula (2) to:

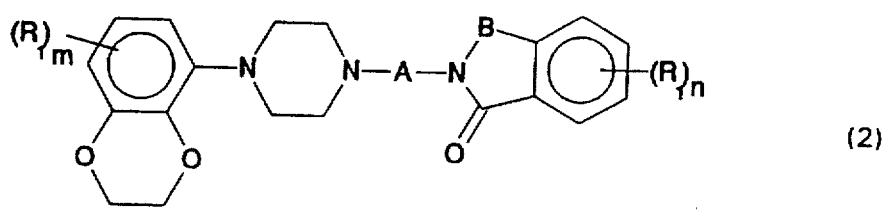

(2)

column 1, change formula (1) to:

(1)

UNITED STATES PATENT AND TRADEMARK OFFICE
CERTIFICATE OF CORRECTION

Page 2 of 2

PATENT NO. : 5,462,942
DATED : October 31, 1995
INVENTOR(S) : HARTOG et al

It is certified that error appears in the above-indentified patent and that said Letters Patent is hereby corrected as shown below:

column 2, change formula (3) to:

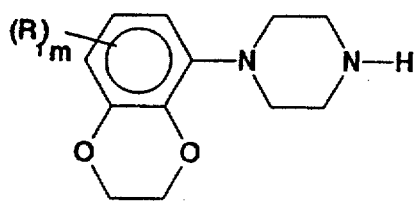

(3)

Signed and Sealed this

Fifteenth Day of July, 1997

Attest:

BRUCE LEHMAN

Attesting Officer

Commissioner of Patents and Trademarks